(12) United States Patent
Kunze et al.

(10) Patent No.: US 8,129,725 B2
(45) Date of Patent: Mar. 6, 2012

(54) SEMICONDUCTOR SENSOR

(75) Inventors: Mike Kunze, Pfaffenhoffen (DE); Ingo Daumiler, Dietenheim (DE)

(73) Assignee: MicroGan GmbH, Ulm (DE)

( * ) Notice: Subject to any disclaimer, the term of this patent is extended or adjusted under 35 U.S.C. 154(b) by 520 days.

(21) Appl. No.: 12/063,366

(22) PCT Filed: Aug. 8, 2006

(86) PCT No.: PCT/EP2006/007846
§ 371 (c)(1),
(2), (4) Date: May 9, 2008

(87) PCT Pub. No.: WO2007/017252
PCT Pub. Date: Feb. 15, 2007

(65) Prior Publication Data
US 2010/0133547 A1    Jun. 3, 2010

(30) Foreign Application Priority Data
Aug. 8, 2005 (DE) .................. 10 2005 037 276

(51) Int. Cl.
*H01L 29/12* (2006.01)
(52) U.S. Cl. ............ 257/76; 257/77; 257/192; 257/197; 257/E29.091; 257/E29.068; 257/E29.246; 257/E29.188
(58) Field of Classification Search .................. 257/76, 257/77, 429, 192, 197, E29.091, E29.068, 257/E29.246, E29.188
See application file for complete search history.

(56) References Cited

U.S. PATENT DOCUMENTS

| 4,698,657 | A | * | 10/1987 | Watanabe et al. ............. 257/253 |
| 4,910,293 | A | * | 3/1990 | Uekita et al. .................. 528/353 |
| 5,833,824 | A | * | 11/1998 | Benton ......................... 204/416 |
| 6,022,463 | A | * | 2/2000 | Leader et al. ............. 204/403.06 |
| 6,791,738 | B2 | * | 9/2004 | Reynolds et al. ............. 359/265 |
| 7,368,085 | B2 | * | 5/2008 | Gu et al. .................... 422/82.01 |
| 2002/0052076 | A1 | | 5/2002 | Khan et al. |
| 2005/0012115 | A1 | * | 1/2005 | Grueger et al. ............... 257/192 |
| 2005/0040488 | A1 | * | 2/2005 | Chou et al. .................... 257/428 |
| 2005/0097941 | A1 | | 5/2005 | Sandvik et al. |
| 2005/0110053 | A1 | | 5/2005 | Shur et al. |

(Continued)

FOREIGN PATENT DOCUMENTS
DE        10062044        6/2002

OTHER PUBLICATIONS

Chou et al.,"Study on the Temperature Effects of Al2O3 Gate pH-ISFET," Sensors and Actuators, Elsvier Science B. V., B81, 2002, pp. 152-157.

(Continued)

*Primary Examiner* — Allan R Wilson
(74) *Attorney, Agent, or Firm* — Fay Kaplun & Marcin, LLP.

(57) ABSTRACT

A semiconductor sensor determines physical and/or chemical properties of a medium, in particular a pH sensor. The semiconductor sensor has an electronic component with a sensitive surface, said component being constructed for its part on the basis of semiconductors with a large band gap (wide-gap semiconductor). The sensitive surface is provided at least in regions with a functional layer sequence which has an ion-sensitive surface. The functional layer sequence has at least one layer which is impermeable at least for the medium and/or the materials or ions to be determined.

41 Claims, 7 Drawing Sheets

U.S. PATENT DOCUMENTS

2005/0228313 A1\* 10/2005 Kaler et al. ................... 600/583
2007/0086916 A1\* 4/2007 LeBoeuf et al. ................ 422/58
2008/0174494 A1\* 7/2008 Suzuki et al. .......... 343/700 MS
2009/0220381 A1\* 9/2009 McGimpsey ................ 422/68.1

OTHER PUBLICATIONS

Spetz et al., "Current Status of Silicon Carbide Based High-Temperature Gas Sensors," IEEE Transactions on Electron Devices, vol. 46, No. 3, Mar. 1999, pp. 561-566.

\* cited by examiner

Fig. 6

SEMICONDUCTOR SENSOR

FIELD OF INVENTION

The present invention relates to a semiconductor sensor for determining physical and/or chemical properties of a medium. There are thereby termed as medium fluids, in particular liquids or gases. The present invention relates in particular to a pH sensor for determining the pH value of a liquid. Sensors of this type are based on electronic semiconductor components, in the present case based on so-called "wide band gap semiconductors", or semiconductors with a large band gap, the band gap being >2 eV. Semiconductors of this type are present for example in the material systems gallium nitride (GaN) or diamond. There are suitable as embodiments for the semiconductor components, in particular field effect transistors, for example HEMT, MODFET, MESFET or also so-called δ-FET (volume semiconductors with a pulsed doping concentration profile). However basically all semiconductor materials are suitable as volume material for electronic components of this type.

BACKGROUND INFORMATION

There is understood by HEMT a high electron mobility transistor, by MODFET a modulation-doped field effect transistor, by MESFET a metal semiconductor field effect transistor, by δ-FET a MESFET, in the case of which a doping pulse with a high concentration has been placed near the surface, by SIT a static induction transistor and by HBT a heterostructure bipolar transistor (heterojunction bipolar transistor).

An ion-sensitive semiconductor sensor of this type is shown for example in DE 100 62 044 A1. This sensor has a field effect transistor with a heterostructure comprising group III nitrides which is configured as a HEMT structure. The uppermost layer of the layer sequence is in direct contact with the medium to be measured during the measurement. Alternatively, a functional layer can be applied on the uppermost layer of the layer sequence, said functional layer selectively allowing through the specific ions to be determined. In every case, the ions which have been allowed through strike the gate surface or GaN surface of the layer sequence and immediately initiate the sensor effect there. There are proposed as functional layers of this type, in particular ion exchangers, such as e.g. zeolites.

In the case of pH sensors, it is proposed to apply a conducting ceramic which is selectively permeable for ionised hydrogen atoms onto the uppermost layer of the components. Suitable materials for this purpose are materials known by the name ormocers.

In fact, in principle a III-V semiconductor, such as GaN or AlGaN, is exceptionally suitable because of its polarity and surface charges for achieving a pH sensitivity relative to solutions or other media. It is disadvantageous with these pH sensors, as described also above for the state of the art, that the signals are not however reproducible and in particular a pH sensor of this type is not chemically resistant.

SUMMARY OF INVENTION

It is therefore the object of the present invention to make available a semiconductor sensor for determining physical and/or chemical properties of a medium which, on the basis of semiconductors with a large band gap, produces stable and reproducible signals.

According to the invention, the semiconductor sensor has an electronic component with a sensitive surface. The electronic component is constructed on the basis of semiconductors with a large band gap, in particular on the basis of III-V semiconductors. According to the invention, the sensitive surface is now coated at least in regions with a functional layer sequence, the functional layer sequence having, for its part, an ion-sensitive surface but being impermeable for the medium and/or the ions or materials to be determined.

Furthermore, it is substantially advantageous here if the uppermost layer of the functional layer sequence is chemically resistant. Furthermore, it is substantially advantageous if at least one of the layers of the functional layer sequence acts as an at least ion-selective diffusion barrier layer for the ions to be determined.

There are used particularly advantageously for the semiconductor sensors according to the invention, semiconductors with a large band width, such as for example diamond, gallium nitride (GaN) or silicon carbide (SiC). However, it has been shown in experiments for the material system GaN that, when using an untreated GaN-based surface in the case of which for example the uppermost layer comprises AlN, GaN, $Al_xGa_{1-x}N$ or other compounds, no stable and reproducible functionality is achieved in contact with the medium to be examined. The causes for this have to date not been explained. Similar difficulties result when using pure, in particular hydrogen-terminated or only partially oxygen-terminated diamond surfaces.

In order to achieve a stable and reproducible functionality for measuring the media, for example gas, liquid or gels or the like, a functional layer or layer sequence is therefore applied according to the invention on the sensitive layer. It merely fulfils the role of a mediator for the surface of the semiconductor component, said layer being impermeable for example for the ions or materials themselves to be measured, for example hydrogen ions.

The electronic components can be constructed laterally or also vertically. There are suitable for this purpose diverse types of transistors, for example HEMT, MODFET, MESFET, δ-FET or also HBT. The gate electrode is thereby formed by the sensitive surface of the electronic component if necessary in conjunction with the medium located above the functional layer sequence.

For the sensitive surface of the electronic component, there are suitable as materials aluminum nitride, gallium nitride, indium nitride or aluminum gallium nitride of the formula $Al_xGa_{1-x}N$ or indium gallium nitride of the formula $In_xGa_{1-x}N$, there applying $0.01 \leq x \leq 0.3$. There is suitable as further material also indium aluminum nitride $In_xAl_{1-x}N$, there applying here $0<x<1$.

For the uppermost layer or another layer of the functional layer sequence which is intended as far as possible to be chemically inert, chemically resistant and impermeable for the medium or ions or materials, there are suitable oxides, in particular metal oxides, such as titanium oxide ($TiO_2$), aluminum oxide ($Al_2O_3$), magnesium oxide (MgO), iron oxide ($Fe_2O_3$), chromium-titanium oxide ($Cr_{1.8}Ti_{0.2}O_3$), tungsten oxide ($WO_3$), indium oxide ($In_2O_3$) or lanthanum-iron oxide ($LaFeO_3$) or metals, ceramic or nitride-based materials such as titanium nitride or silicon nitride. Also carbon-containing compounds, such as diamond or diamond-like carbon (DLC) are suitable for this purpose. An oxide layer is particularly suitable if this is produced by thermal oxidation of a previously applied layer, by electrochemical deposition and/or by sputter deposition of the oxide itself as layer.

A bonding layer can be disposed between the functional layer sequence and the electronic component in order better to bond the functional layer sequence to the electronic component. There are suitable for the bonding layer materials such as titanium, aluminum, titanium tungsten alloys, silicon or various polymers.

The entire sensor can be encapsulated with the exception of its sensitive surface. This can be effected for example by casting in epoxy resin and/or in polyimides.

The electronic component can be disposed directly or above intermediate layers on a substrate, for example comprising silicon, sapphire, silicon carbide, diamond, iridium or the like. Between substrate and component, in addition a buffer intermediate layer, for example comprising gallium nitride, aluminum nitride, aluminum gallium nitride, diamond and/or combinations thereof, can be disposed. The electronic component is disposed possibly on a carrier for improved handling, for example by gluing, soldering and/or flip-chip technology.

Furthermore, electrical external contacts are provided with which the sensor signal can be conducted away. The semiconductor sensor according to the invention is outstandingly suitable for relative and absolute measurements of chemical and/or physical parameters.

For further improvement in the sensor accuracy, two similar sensors can be disposed together on a substrate or carrier. Thus, a plurality of signals can be achieved, via which possibly averaging can take place.

It is a further possibility to cover one of the thus disposed plurality of sensors on its sensitive surface with an inert material. This sensor is consequently not influenced by the medium and can therefore be used for determining other, non-sensor-relevant values, for example for determining the temperature and its influence on the sensor signal.

The sensors according to the invention are suitable in particular for determining the $H^+/H_3O^+$ concentration or the $OH^-$ concentration, i.e. as pH sensors, or for determining the $O_2$ concentration, i.e. as oxygen sensors.

The sensors according to the invention are suitable not only for measuring in the range of room temperature, but in particular even at higher temperatures between 50° C. and 500° C., in particular in the range between 150° C. and 450° C.

Some examples of semiconductor sensors according to the invention are described in the following. The same or similar reference numbers are thereby used for the same and similar elements. Furthermore, the subsequent description of the examples of semiconductor sensors according to the invention should be understood such that not only all the features described in one example in combination with each other are claimed as a unit but also the individual features in further combinations, not cited here in detail, are together or individually per se part of the present invention.

DETAILED DESCRIPTION

Figure 1:
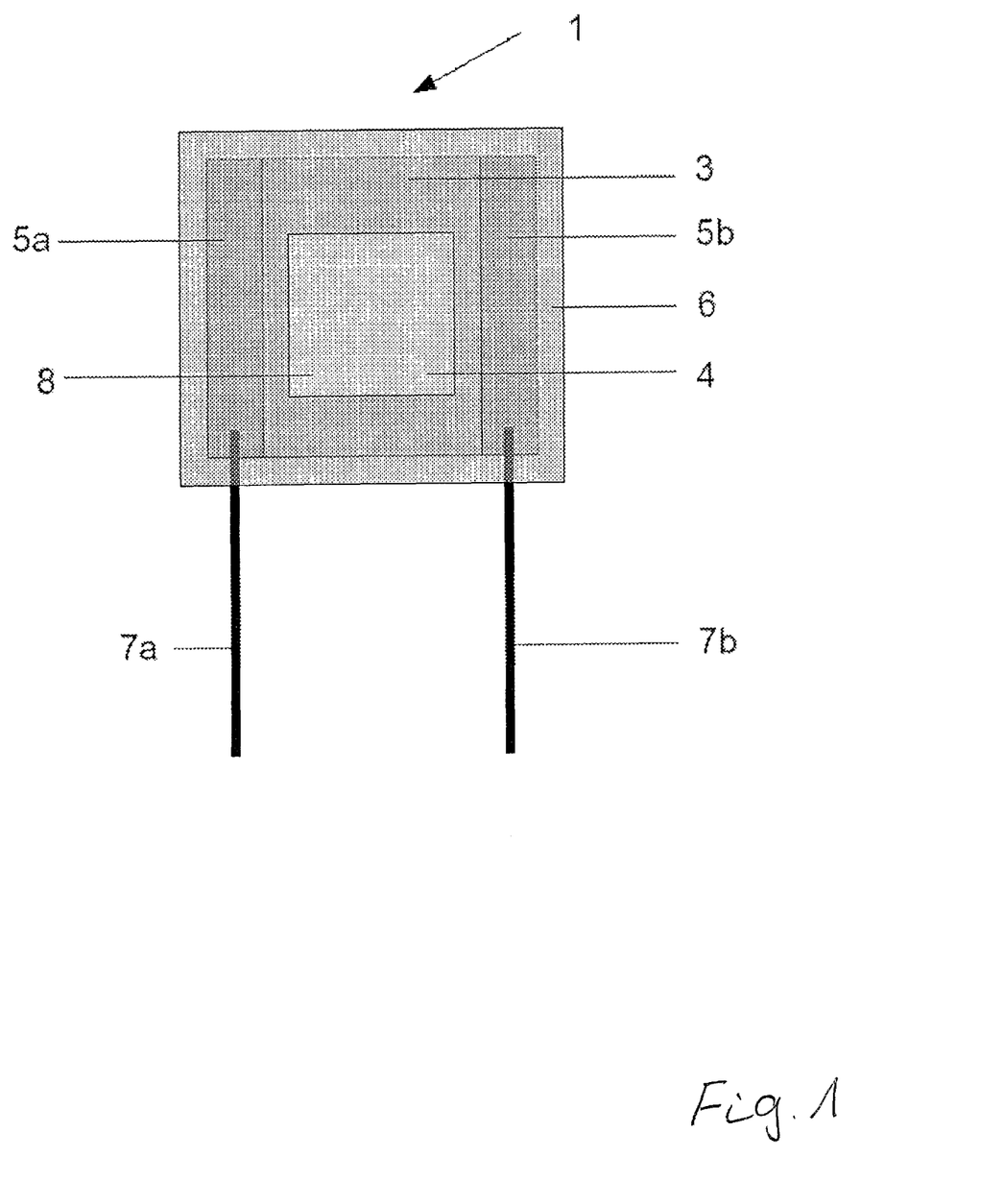
FIG. 1 shows a semiconductor sensor according to an exemplary embodiment of the present invention.

FIG. 1 shows a semiconductor sensor 1 as ion sensor in cross-section in plan view.

The semiconductor sensor 1 has a semiconductor material 3. There are located laterally at two oppositely situated sides of the semiconductor material 4 which is rectangular in cross-section, electrical contacts 5a, 5b at which the generated sensor signal is present. These contacts 5a and 5b are typically ohmic contacts but can also be configured as blocking contacts. The semiconductor material 3 is packed with a material 6 which is resistant relative to the medium to be measured and in addition insulating. For this purpose, for example an epoxy resin can be used. Only the region 8 is left free of this insulation so that the region 8 represents an opening in which the semiconductor material can come in contact with the medium to be examined. In this region 8, the semiconductor material is however coated with a functional layer 4 so that this contact is merely indirect. The material of this functional layer 4 is thereby as far as possible chemically inert and impermeable for ions.

Several types can be differentiated for the functional layer 4, which differ with respect to their permeability relative to specific ions from the medium to be examined and differentiated also via the number of layers of this system. In the present invention, layer systems which are overall impermeable for ions are preferred, this implying for a single-layer system a layer which is totally impermeable for ions, whilst, in the case of multilayer systems, merely at least one or some layers should be impermeable at least for the ions to be determined, whilst other layers can be partially or entirely permeable for ions or other materials.

The mode of operation of the functional layer 4 can be explained as follows: it should enable a chemical bonding of ions from the medium to be examined but prevent passage to the semiconductor surface entirely or partially. As a result of the chemical bonding, the conversion of the chemical concentration at least of one component of the medium is effected into an electrical value, for instance the potential on the surface of the functional layer and hence, as a consequence, changes an electrical characteristic value (for instance the potential) on the semiconductor surface of the component itself. This has an effect on the semiconductor and is used to cause an electrical change (for example the charge carrier density or spatial charge zone and hence finally the current and/or the capacitance) in the semiconductor.

As functional layer sequence 4, different materials, such as for instance oxides, nitrides, metals or ceramics and also the respective oxides, mixtures, stoichiometric or non-stoichiometric compounds or alloys, can be used.

Preferably, this functional layer sequence comprises a multilayer system, each layer undertaking specific tasks. For example, a three-layer system can be chosen in which the lowermost layer (directly in contact with the semiconductor) serves as bonding agent (can be for instance titanium or Al or TiW, Si, polymer, or the like). The central layer is chosen such that diffusion of at least specific or even of all the ions towards the semiconductor surface is prevented. The uppermost layer (in direct contact with the medium to be examined) can be chosen freely in order to achieve a high effective selectivity for specific ions or quantities. This can be for example titanium oxide, Si oxide, Al oxide, Si nitride (respectively stoichiometrically or also non-stoichiometrically) or even be a metal, such as platinum, or a compound. The corresponding thicknesses of the layers are chosen at least to be so high that their function is fulfilled but to be as thin as possible in order to ensure a potential transmission to the semiconductor surface which is as low-loss as possible. Likewise, these layers can be structured in order to make individual layers accessible specifically in specific regions from the surface (for example in order to produce an electrical contact to a layer.

It is revealed that both titanium oxide applied by sputter deposition or electrical deposition and by subsequent oxidation of titanium layers applied on the semiconductor surface, with thicknesses between 5 nm and 20 nm, allow a functionality of the sensors to be achieved in particular for determining pH values.

The layers produced by subsequent oxidation must in addition have no stoichiometric compound or be present for instance preferably in a specific crystallinity but can be characterised for example preferably by an excess of one component (for instance oxygen or nitrogen relative to the metal). This can be used specifically in order to adjust for instance the dielectric constant or the electrical resistance.

Furthermore, resistance to lyes and acids and also to a multiple CIP test cycle (clean-in-place test cycle) using NaOH and $HNO_3$ was able to be established on the mentioned titanium oxide layers. Hence application possibilities are opened up in the field for instance of foodstuff production or in the pharmaceutical industry. By using the wide band gap semiconductor, the operation is also possible at temperatures above room temperature, for instance at temperatures between 50° C. and 500° C., preferably in the range 150° C. to 450° C.

In combination with the functional layer 4, there are particularly suitable semiconductor structures 3 which deliver a high signal response with low potential change under the prescribed conditions, such as for instance specific operating current or voltage (in order for example to avoid heating effects or to enable an operating voltage below the dissociation voltage of the medium to be examined):

1. In the case of for example AlGaN/GaN-HEMT, the electrically active layer 3 comprises for example at least two layers: a lower GaN— and an upper AlGaN layer. Structures are preferred which have a comparatively low Al content x, relative to normal AlGaN/GaN transistors, between 1% and 15% with a low thickness of the AlGaN layer (here typically between 0 and 20 nm, otherwise 20 to 30 nm are normal). The lower Al content leads to moderate charge carrier layer concentrations (not as normal in the range $10^{13}$ $cm^{-2}$ but in the range $10^{12}$ $cm^{-2}$) and hence also to earlier current saturation (i.e. current saturation with lower supply voltage, here for instance already below 4 V). The lower thickness is jointly responsible via its influence on the conduction band discontinuity for the comparatively lower charge carrier layer concentration and the lower cut-off voltage of the component. In total, a higher sensitivity of the semiconductor component to potential changes on the surface can hence be achieved.
2. In the case of volume semiconductors, these are for example structures in the material system GaN or diamond which
   a) are either slightly volume-doped (activated charge carrier concentration in the range below $5*10^{17}$ $cm^{-3}$) with a thickness of the electrically active layer 3 in the range 10 to 500 nm or
   b) have a pulse doping (with activated charge carrier layer concentration in the range below $10^{13}$ $cm^{-2}$) in the volume material of the electrically active layer 3 below the semiconductor surface. The gap to the semiconductor surface should thereby be in the range 2 nm to 20 nm in order to achieve a high sensitivity.

It is hereby essential that the functional layer sequence 4 itself does not serve as gate insulator or gate oxide, as is the case for example with a silicon-MOS system which is used in classical ISFET or CHEMFET applications. The gate oxide in silicon systems of this type is absolutely necessary for the component function per se. In the present case, the functional layer is however decoupled from the function of the electronic component which is implemented in the semiconductor material 3.

Accordingly, the sensitive surface should also not be regarded directly as gate electrode or merely in connection with the medium to be measured. In fact this determines for example, in a pH sensor, the proportion of $OH^-$ or $H^+$ ions and hence the potential present at the surface of the functional layer 4. This potential then determines for its part the current flow between for example the source electrode and the drain electrode of the electronic component.

It is therefore also possible, with the help of an electrode for example made of platinum, to apply an additional potential to the surface via the solution in order to control the electronic component, for example a field effect transistor, or to define an operating point. A reference electrode, the potential of which is always constant relative to the solution, is thereby preferred.

In this example, the functional layer advantageously comprises titanium oxide. The encapsulation of the sensor with the external insulation 6 is not required everywhere, in particular not if the material properties of the semiconductor material 3 allow this entirely or partially. It can then suffice already to apply the covering 6 only on the required regions, for instance only on the regions surrounding the contact region 8 or on the terminals 5a, 5b.

Also the shaping of the electrical contacts 5a, 5b can be adapted to the respective measuring method. The basic form thereby resides in a rectangular format for the contacts 5a, 5b, as can be seen in FIG. 1. For capacitive measurements on planar structures, also a round structure can however be preferred. Acute-angled or punctiform contact geometries can also be used, for instance in order to produce specifically local high field zones of an electrical field. The entire sensor 1 can for its part be disposed on one carrier. This can be effected for example by glueing, soldering or flip-chip technology. This then enables integration in a circuit. For example, strip conductors on a carrier material can then be used which, by means of a technology such as lithography, can be contacted in conjunction with metallisation, glueing, soldering, bonding or the like to the contacts 5a and 5b in order to produce an electrical contact of the sensor 1 to the measuring environment or to the electronic evaluation unit.

In FIG. 1, two electrical contacts 5a, 5b are represented. However a structure is also conceivable which has merely one electrical contact on the semiconductor material 3, a possible second contact being able to be established via a counter-electrode in the medium to be measured.

As a rule, a counter-electrode is dispensed with however during determination of the pH value since the counter-electrode possibly itself has a pH dependency and hence precise determination of the pH value is not possible. Instead, a reference electrode which is pH-independent can be used, irrespective of how the pH sensor is wired. The reference electrode thereby always has the same potential relative to a solution, irrespective of the pH value of the solution. With the help of a reference sensor of this type and the pH sensor, the pH value of an unknown solution can be determined. A counter-electrode is therefore merely required if the transistor is intended to be controlled via the solution or in order to characterise the pH sensor. However this is always effected with a known pH solution.

Furthermore, the embodiment of one or more of the electrical contacts 5a, 5b as a non-blocking contact is just as possible as a blocking contact and also a combination of blocking with non-blocking contacts.

In the case of a pH sensor, as was also represented in this Figure, two measuring methods are possible.

On the one hand, the change in drain source current at a constant drain source voltage can be measured. On the other hand, the change in drain source voltage at a constant drain source current can be measured.

Figure 2:
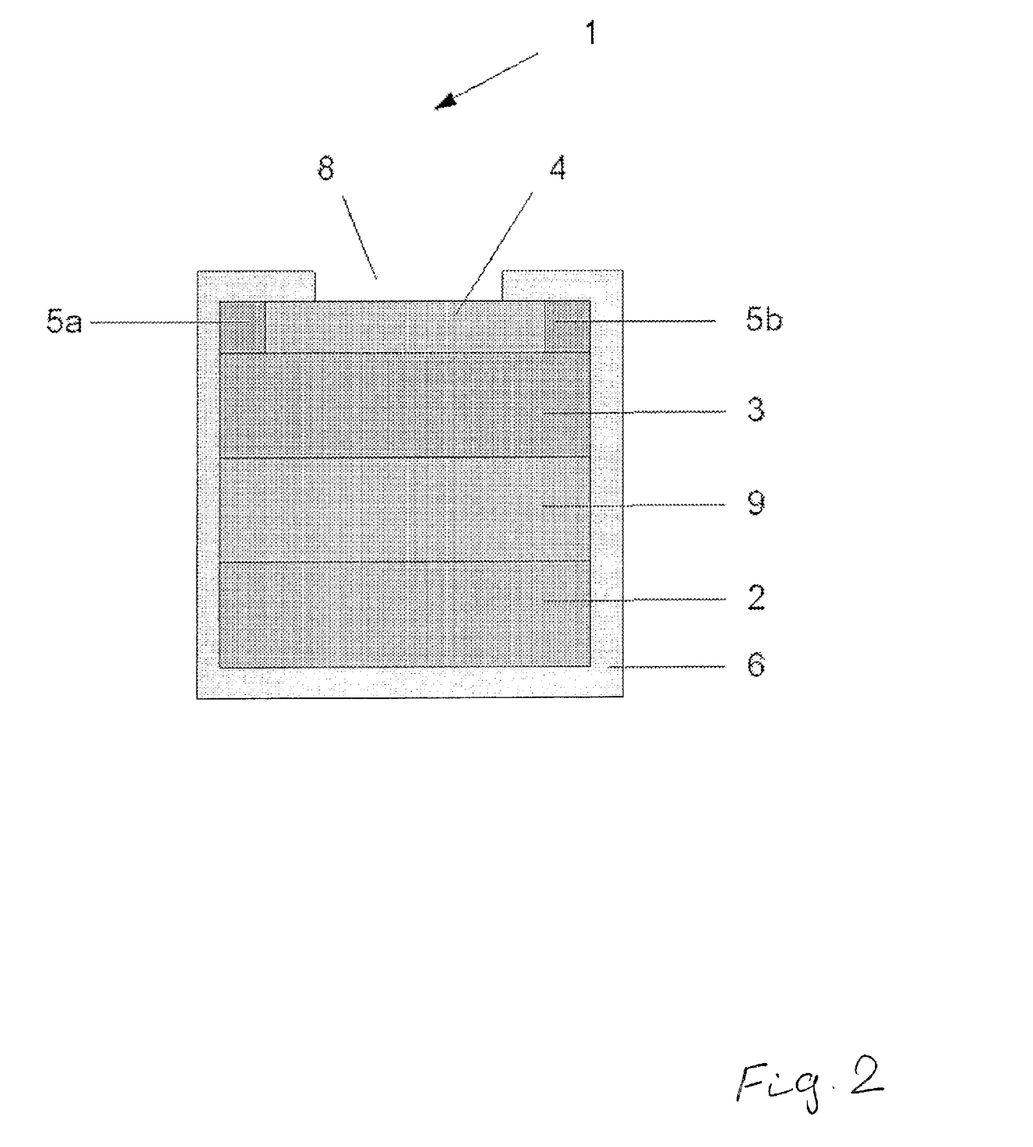
FIG. 2 shows a cross-section of a corresponding semiconductor sensor according to an exemplary embodiment of the present invention.

FIG. 2 shows a further example of a sensor according to the invention. This is now shown in cross-section so that the layer construction underneath the functional layer 4 can be detected. On a substrate 2 which, in this example, comprises silicon, sapphire, silicon carbide, diamond or iridium, a buffer layer 9 is located, for example comprising gallium nitride, aluminum nitride, aluminum gallium nitride or diamond. A further layer sequence 3, for example GaN/AlGaN/GaN or doped GaN, forms the electronic component. On the surface of this electronic component 3 there are now located the electrical contact structures 5a, 5b which laterally delimit a functional layer sequence 4 comprising a plurality of layers.

The layer sequence comprising the layers 2, 9, 3, 5a, 5b and 4 is packed by an electrically insulating material 6, merely one opening 8 on the surface of the functional layer sequence 4 as sensitive layer not being covered and hence remaining open. Through this opening 8, the medium to be examined can come in contact with the surface of the functional layer sequence 4.

Figure 3:
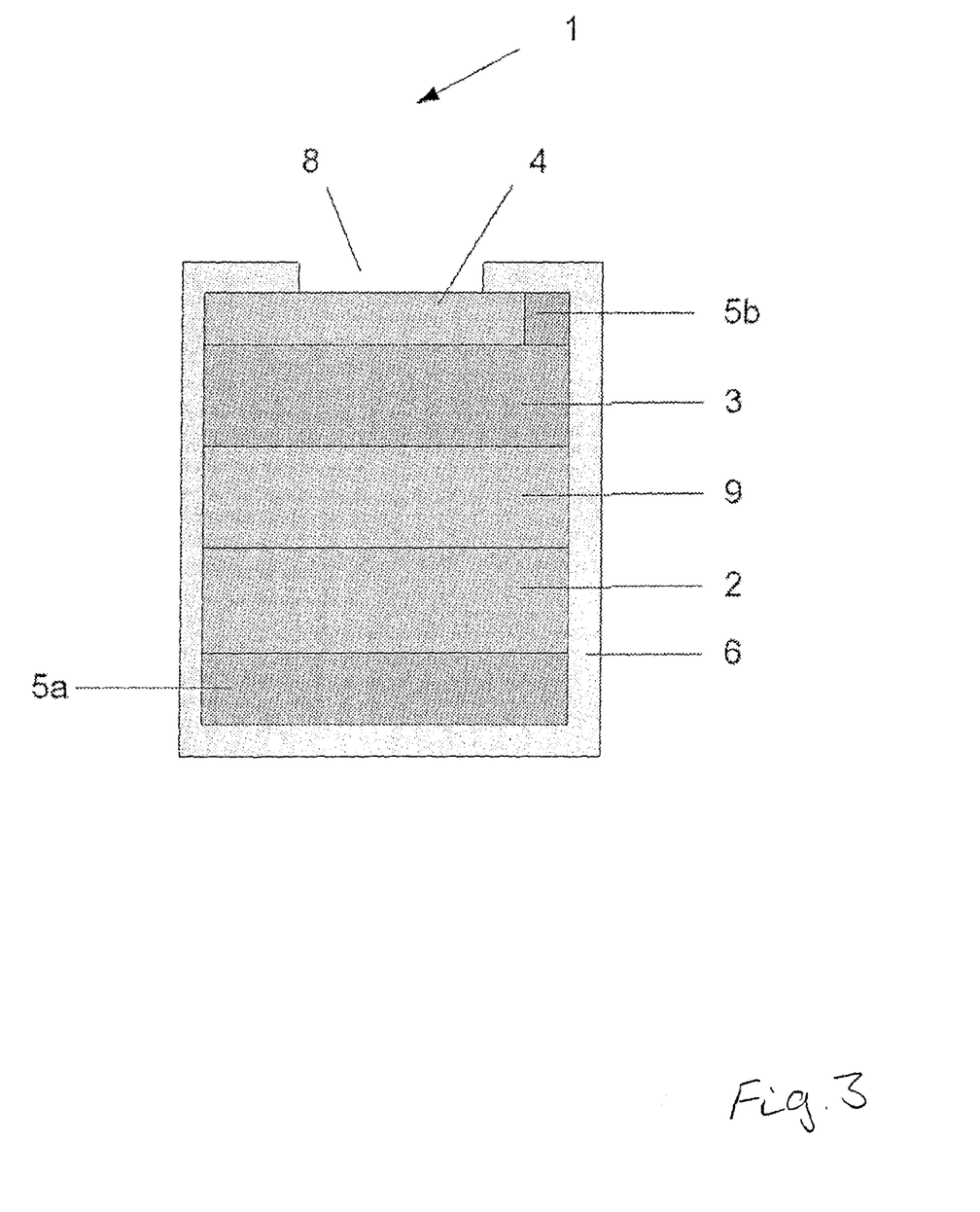
FIG. 3 shows a cross-section through a further sensor according to an exemplary embodiment of the present invention.

FIG. 3 shows a vertical construction of a sensor, the layer sequence corresponding to that in FIG. 2. A vertical construction of this type can be used for example with bipolar transistors SiT or the like. The electrical contacts 5a, 5b are therefore located preferably on the upper side or underside or also upper- and underside or, in the case of etched structures, on one side but in different layers or etch depths. Also a deep etching of local regions of the upper- and underside of the layer sequence can be used.

Figure 4:
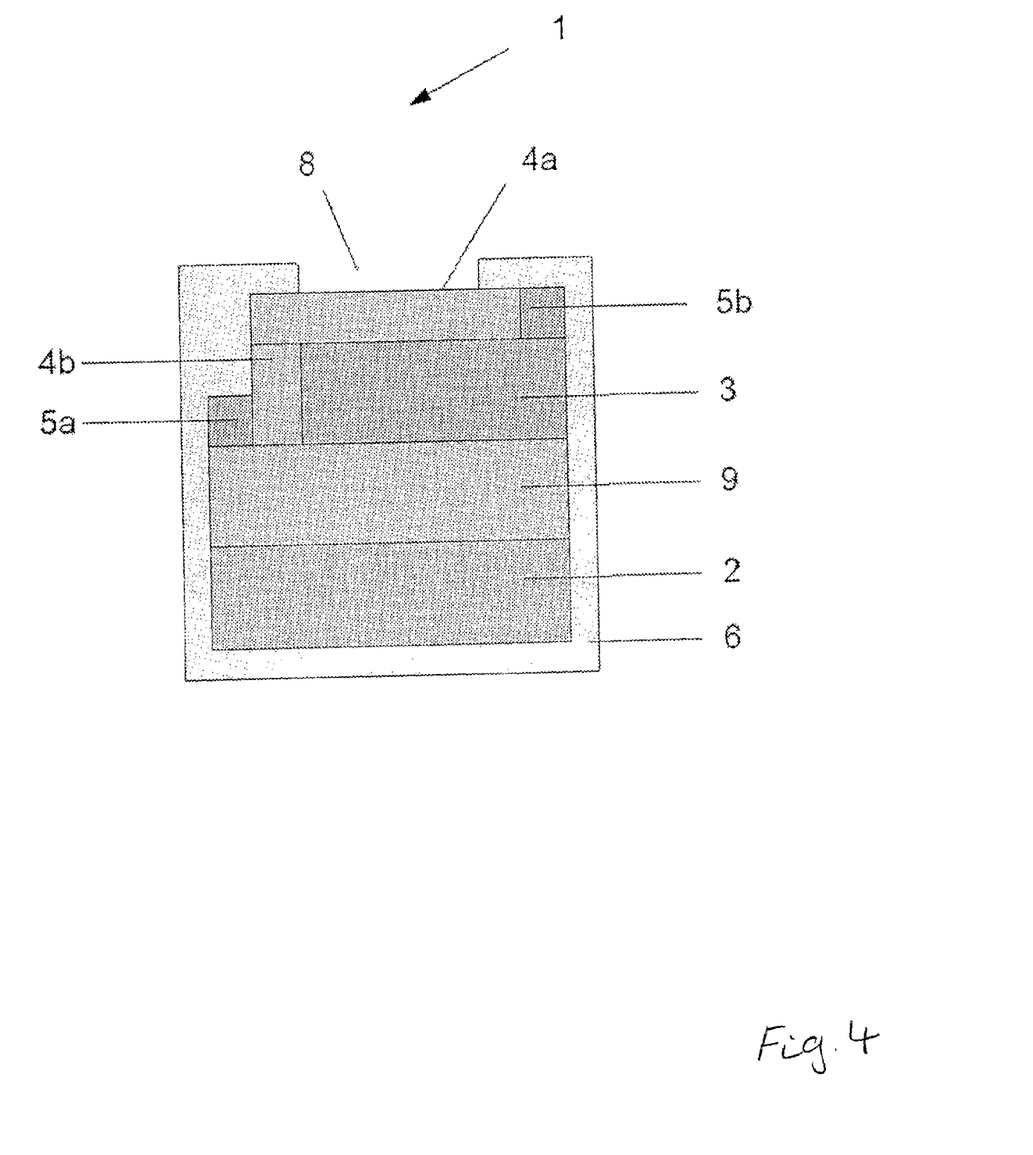
FIG. 4 shows a cross-section through a further sensor according to an exemplary embodiment of the present invention.

A sensor of this type is shown for example in FIG. 4. In this sensor, again the layer sequence comprising the layer substrate 2, buffer 9 semiconductor 3 and layer sequence 4a is corresponding to that in FIG. 2. The layer sequence 4a has however an adjacent layer sequence 4b which extends in the vertical direction. Here the contact 5a essentially contacts the buffer layer 9 and the layer sequence 4b whilst the contact 5b contacts the electronic component 3 and the layer sequence 4a.

Figure 5:
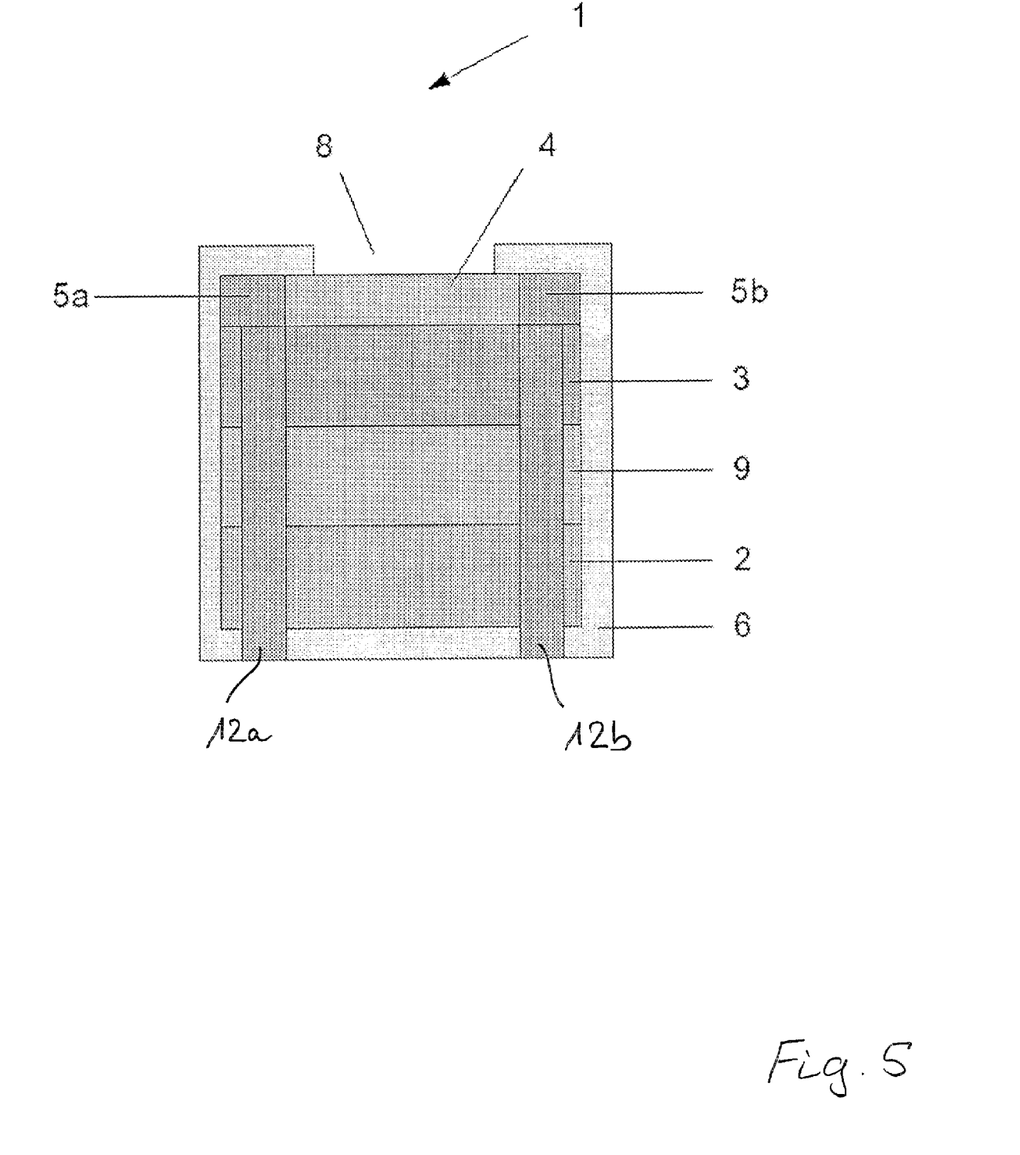
FIG. 5 shows a cross-section through a further sensor according to an exemplary embodiment of the present invention.

FIG. 5 shows a further sensor structure in which again the layer sequence comprising substrate 2, buffer 9 and semiconductor material 3 and also layer sequence 4 corresponds to that in FIG. 2. The contacts 5a and 5b are likewise disposed laterally of the layer sequence 4, as in FIG. 2. However, they are connected to electrical connections 12a, 12b which for their part are introduced in the layer sequence in the vertical direction. In this way, it is possible to contact the sensor on its rear-side which is orientated away from the sensitive surface and the opening 8. A rear-side contacting of this type enables the contacting and placing of the sensor on a board or carrier without requiring to provide contactings on the front-side of the sensor. It is therefore possible here directly to contact electrical lines applied on the board or carrier, for example the conductor of a printed circuit board.

Figure 6:
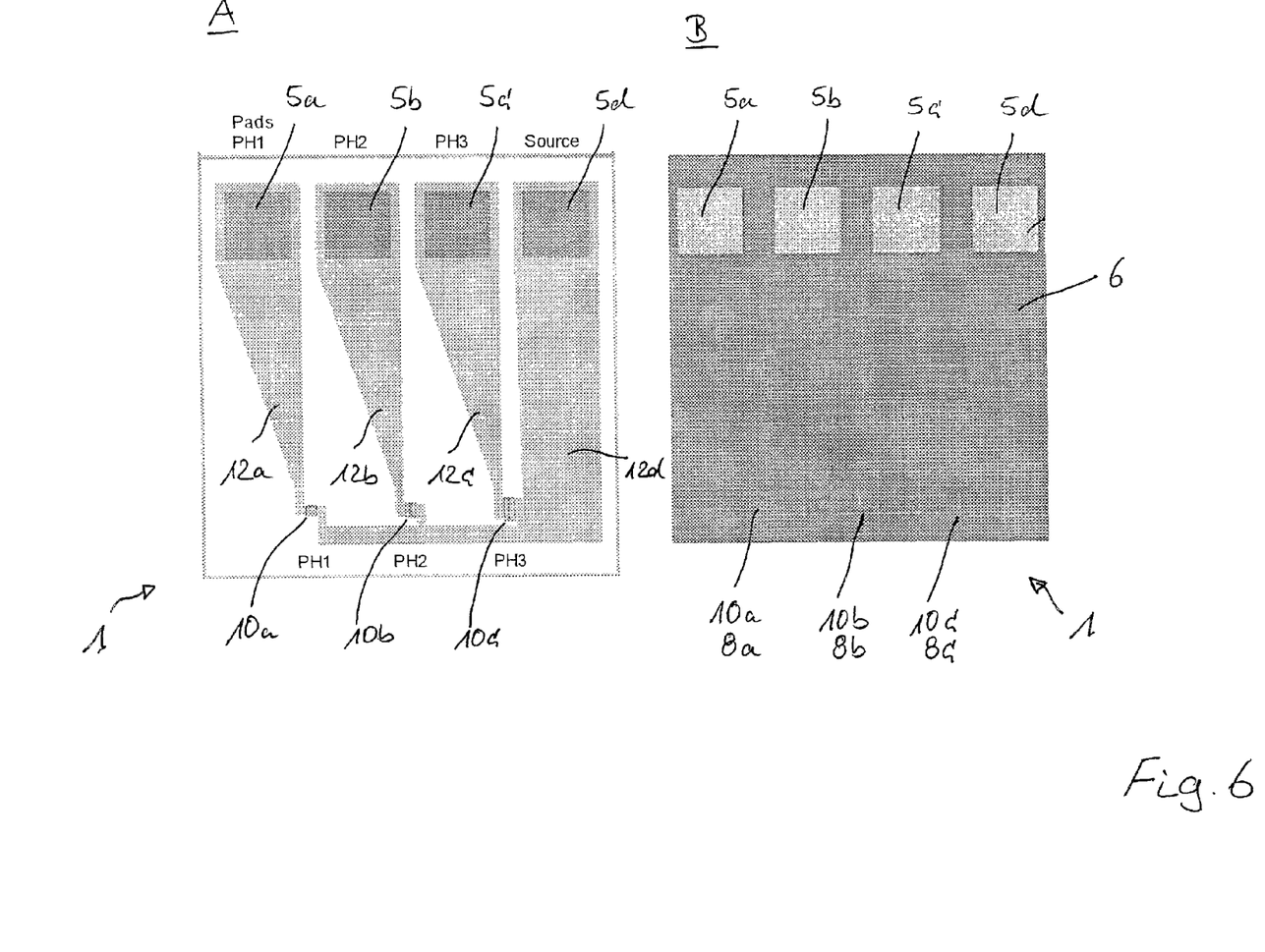
FIG. 6 shows a cross section and a plan view on a further sensor according to an exemplary embodiment of the present invention with a plurality of sensor elements.

FIG. 6 shows, in the partial pictures A and B, a further sensor according to the invention which has individual sensor elements. In FIG. 6A, a cross-section in plan view on the sensor can be detected. The sensor has in total three sensor elements 10a, 10b, and 10c which are connected via electrical lines 12a, 12b, 12c and 12d to contacts 5a, 5b, 5c and 5d. The contact 5d is earthed whilst the contacts 5a, 5b and 5c can be connected to a voltage source.

The geometries of the sensor elements 10a, 10b, 10c, which are jointly formed by the sensitive surfaces of the functional layers 4 according to the invention, are different with respect to their size from the example shown in FIG. 6. They can also be different with respect to further properties so that the individual sensor elements respond to different ions or materials in a further different manner. The individual sensor elements can therefore have the same function or different functions (delicacy, sensitivity etc.).

As can be detected in FIG. 6B in plan view on the finished sensor, the surface of the sensor 1 is most extensively covered with an electrically insulating material 6. Not covered by the material 6 are the contacts 5a, 5b, 5c and 5d and also the openings 8a, 8b and 8c which enable access of the medium to the sensor elements 10a, 10b and 10c.

The overall dimension of the sensor element array 1, in the present example, is 5 mm×5 mm, whilst the sensor surfaces which are determined by the sizes of the opening 8a, 8b and 8c are, for the opening 8a 10 μm×50 μm, for the opening 8b 10 μm×100 μm and for the opening 8c 10 μm×200 μm. In this example, a polyimide was used as covering material 6.

As can be detected easily, the present invention enables extensive miniaturisation of the sensors and hence also diversity of the measuring options.

Figure 7:
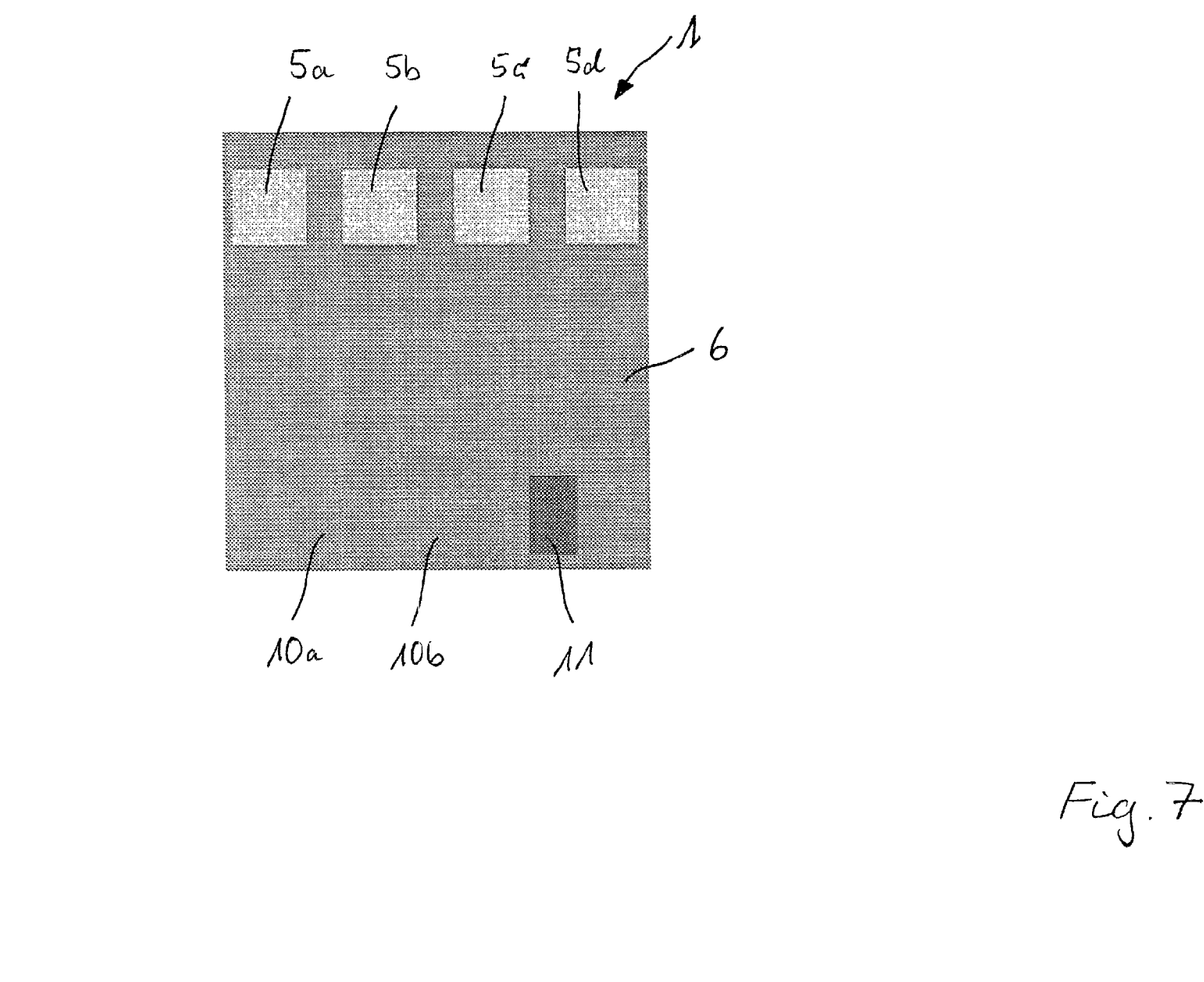
FIG. 7 shows the plan view on a further semiconductor sensor according to an exemplary embodiment of the present invention.

FIG. 7 shows a further sensor which is similar to that in FIG. 6. In contrast to the sensor shown in FIG. 6B, the opening 8c of the sensor element 10c is however covered. As a result, the sensor element 10c displays no sensitivity to media and is a blind sensor. With respect to all the other parameters, this blind sensor element has however the same construction and the same structure as a normal sensor.

By means of the sensor element 10c, it is now possible to determine changes in sensor sensitivity of the sensor elements 10a and 10b etc. on the basis of temperature change or other factors and to calibrate the normal sensor elements 10a and 10b which measure the medium or their signals correspondingly. Due to this blind sample, it is therefore possible by means of the covered sensor element 10c to compensate for other disruptive influences.

The invention claimed is:

1. A semiconductor sensor for determining at least one of physical properties and chemical properties of a medium, comprising:
an electronic component with a sensitive surface, the sensitive surface comprising semiconductors with a large band gap,
wherein the electronic component is a transistor, a gate electrode of the transistor being formed with the sensitive surface, and
wherein the sensitive surface, at least in regions coated with a functional layer sequence with at least one layer, has a functional layer with an ion-sensitive surface, the ion-sensitive surface being orientated away from the sensitive surface of the electronic component, the functional layer sequence preventing passage to the sensitive surface of at least one of (a) the medium and (b) one of materials and ions to be determined.

2. The semiconductor sensor according to claim 1, wherein the sensor is a pH sensor.

3. The semiconductor sensor according to claim 1, wherein an uppermost layer of the functional layer sequence is chemically resistant.

4. The semiconductor sensor according to claim 2, wherein an uppermost layer of the functional layer is resistant to at least one of lyes and acids.

5. The semiconductor sensor according to claim 4, wherein the lyes include sodium hydroxide (NaOH) and the acids include nitric acid (HNO3).

6. The semiconductor sensor according to claim 1, wherein an uppermost layer of the functional layer comprises a material that includes at least one of an oxide, a metal oxide, a titanium oxide, an aluminum oxide, a magnesium oxide, a metal, a ceramic, a nitride-based material, carbon-containing compounds, and mixtures thereof.

7. The semiconductor sensor according to claim 6, wherein each of the at least one of the compounds and the components of the material has a stoichiometric ratio.

8. The semiconductor sensor according to claim 6, wherein the nitride-based material includes at least one of titanium nitride and silicon nitride.

9. The semiconductor sensor according to claim 6, wherein the carbon-containing compounds includes at least one of diamond and diamond-like carbon (DLC).

10. The semiconductor sensor according to claim 4, wherein the uppermost layer is an oxide, the layer being produced as a layer by at least one of (a) a thermal oxidation of the surface of a previously applied non-oxidized layer, (b) an electrochemical deposition and (c) a sputter deposition of the oxide.

11. The semiconductor sensor according to claim 4, wherein the uppermost layer is an oxide, the layer being produced as a layer by a thermal subsequent oxidation.

12. The semiconductor sensor according to claim 1, wherein the functional layer sequence has an ion-selective diffusion barrier layer which is impermeable for at least one type of ions.

13. The semiconductor sensor according to claim 1, wherein the functional layer sequence has a bonding layer which is disposed between the component and further layers of the functional layer sequence.

14. The semiconductor sensor according to claim 13, wherein the bonding layer includes at least one of titanium (Ti), aluminum (Al), titanium-tungsten alloy (TiW), silicon (Si) and a polymer.

15. The semiconductor sensor according to claim 1, wherein the semiconductor with a large band gap has a band gap=2 eV.

16. The semiconductor sensor according to claim 15, wherein the semiconductor with a large band gap includes at least one of diamond, gallium nitride (GaN) and silicon carbide (SiC).

17. The semiconductor sensor according to claim 1, wherein the electronic component comprises one of a doped volume material, an undoped volume material, and a heterostructure disposed at least in regions.

18. The semiconductor sensor according to claim 17, wherein the volume material is a III-V semiconductor.

19. The semiconductor sensor according to claim 17, wherein the volume material is gallium nitride (GaN).

20. The semiconductor sensor according to claim 1, wherein the electronic component is one of (a) one of a lateral component and a laterally constructed component and (b) one of a vertical component and a vertically constructed component.

21. The semiconductor sensor according to claim 1, wherein the electronic component is one of a transistor (HEMT), a MODFET (modulation-doped field effect transistor), a metal semiconductor field effect transistor (MESFET, metal semiconductor FET), a d-FET, a SIT (static induction transistor) and a heterostructure bipolar transistor (heterojunction bipolar transistor, HBT), each transistor having a high electron mobility, the gate electrode being formed one of on and by the ion-sensitive surface of the functional layer sequence.

22. The semiconductor sensor according to claim 21, wherein the electronic component has an uppermost semiconductor layer which is orientated towards the functional layer sequence and comprises one of aluminum nitride (AN), gallium nitride (GaN), indium nitride (InN), aluminum gallium nitride, indium gallium nitride, and indium aluminum nitride.

23. The semiconductor sensor according to claim 22, wherein the aluminum gallium nitride has a formula AlxGa1-xN where x is at least 0.01 and at most 0.3, the indium gallium nitride has a formula InxGa1-xN where x is at least 0.01 and at most 0.3, and the indium aluminum nitride has a formula InxAl1-xN where x is greater than 0 and less than 1.

24. The semiconductor sensor according to claim 1, further comprising:
an encapsulation, the surface of the sensor being covered by the encapsulation except in at least parts of the exposed surface of the functional layer sequence.

25. The semiconductor sensor according to claim 24, wherein the surface of the sensor is covered by the encapsulation with the exception at least of parts of electrical contacts.

26. The semiconductor sensor according to claim 24, wherein the encapsulation includes at least one of an epoxy resin and polyimides.

27. The semiconductor sensor according to claim 24, wherein the encapsulation includes at least one of at least one electrically insulating resistant, at least one chemically resistant and a chemically inert material.

28. The semiconductor sensor according to claim 1, wherein the electronic component is disposed one of directly and above intermediate layers on a substrate.

29. The semiconductor sensor according to claim 28, wherein the substrate includes at least one of silicon (Si), sapphire (Al2O3), silicon carbide (SiC), diamond, iridium (Ir) and combinations thereof.

30. The semiconductor sensor according to claim 28, further comprising:
a buffer intermediate layer disposed between the substrate and the electronic component.

31. The semiconductor sensor according to claim 30, wherein the buffer layer includes at least one of gallium nitride (GaN), aluminum nitride (AlN), aluminum gallium nitride (AlGaN), diamond and combinations thereof.

32. The semiconductor sensor according to claim 1, wherein the electronic component has at least one ohmic contact region.

33. The semiconductor sensor according to claim 32, wherein at least one electrical contact is disposed on the electronic component to conduct away electrical signals from the electronic component, at least one of the electrical contacts being connected to at least one of the ohmic contact regions in one of an electrically conductive manner and a semiconductive manner.

34. The semiconductor sensor according to claim 1, wherein the electronic component is disposed on a carrier.

35. The semiconductor sensor according to claim 1, wherein the electronic component is disposed on a carrier together with the substrate.

36. The semiconductor sensor according to claim 34, wherein the carrier is connected to one of the electronic component and the substrate by at least one of glueing, soldering and flip-chip.

37. The semiconductor sensor according to claim 1, wherein in order to conduct signals of the electronic component to the exterior, the electronic component has at least one ohmic contact region and the carrier has at least one strip conductor as electrical contact which is connected to at least one of the ohmic contact regions of the electrical component in one of an electrically conductive manner and a semiconductive manner.

38. The semiconductor sensor according to claim 1, wherein the electronic component and the functional layer sequence are disposed at least twofold on one of the carrier and the substrate.

39. The semiconductor sensor according to claim 38, wherein at least two of the repeatedly-disposed structures are disposed in the layer plane of one of the carrier and the substrate one next to the other.

40. The semiconductor sensor according to claim 38, wherein an ion-sensitive surface of one of the at least two adjacently disposed structures is covered with a further non-sensitive layer.

41. The semiconductor sensor according to claim 6, wherein each of the at least one of the compounds and the components of the material has a non-stoichiometric ratio.

* * * * *